United States Patent [19]

Keil et al.

[11] Patent Number: 4,744,820
[45] Date of Patent: May 17, 1988

[54] CYCLOHEXENONE DERIVATIVES, THEIR MANUFACTURE, AND THEIR USE AS AGENTS FOR REGULATING PLANT GROWTH

[75] Inventors: Michael Keil, Freinsheim; Ulrich Schirmer, Heidelberg; Dieter Kolassa, Ludwigshafen; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 14,542

[22] Filed: Feb. 13, 1987

[30] Foreign Application Priority Data

Feb. 15, 1986 [DE] Fed. Rep. of Germany ....... 3604871

[51] Int. Cl.$^4$ ............................................. A01N 31/06
[52] U.S. Cl. ....................................... 71/123; 568/376; 568/377
[58] Field of Search ................... 71/123; 568/376, 377

[56] References Cited

U.S. PATENT DOCUMENTS 4,560,403  12/1985  Motojima et al. ................ 71/123
4,584,013   4/1986  Brunner .............................. 71/123

FOREIGN PATENT DOCUMENTS 0186118   7/1986  European Pat. Off. ............. 71/123
5390248   8/1978  Japan ................................... 71/123

OTHER PUBLICATIONS

A. A. Akhrem et al., "A New Simple Synthesis of 2-Acylcyclohexane-1, 3-Diones", *Synthesis*, pp. 925-927 (1978).
Solomaa, "The Chemistry of the Carbonyl Group", pp. 188-192, Interscience Publishers, (1966).
Janout et al., J. Org. Chem., vol. 47, pp. 2212-2213 (1982).

*Primary Examiner*—James H. Reamer
*Attorney, Agent, or Firm*—Keil & Weinkauf

[57] ABSTRACT

Cyclohexenone derivatives of the formula

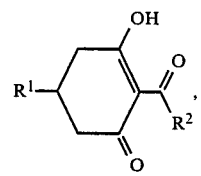

where $R^1$ is —CHO or —CH(OR$^3$)$_2$, $R^2$ is alkyl or alkoxyalkyl, each of 1 to 4 carbon atoms, or cyclopropyl, and $R^3$ is alkyl of 1 to 8 carbon atoms, and salts thereof, processes for their manufacture, and their use as agents for regulating plant growth.

7 Claims, No Drawings

CYCLOHEXENONE DERIVATIVES, THEIR MANUFACTURE, AND THEIR USE AS AGENTS FOR REGULATING PLANT GROWTH

The present invention relates to novel cyclohexenone derivatives, processes for their manufacture, their use as agents for regulating the growth of plants, and a process for regulating plant growth.

It has been disclosed that certain 2-acyl-3-hydroxycyclohex-2-en-1-ones influence plant growth (EP-A-123,001; EP-A-126,713).

We have now found that cyclohexenone derivatives of the formula I

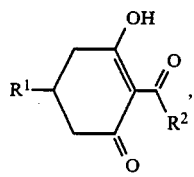

where $R^1$ is —CHO or —CH(OR$^3$)$_2$, $R^2$ is alkyl or alkoxyalkyl, each of 1 to 4 carbon atoms, or cyclopropyl, and $R^3$ is alkyl of 1 to 8 carbon atoms, and salts thereof, exhibit advantageous properties as growth regulators and are well tolerated by crop plants.

Examples of meanings for $R^1$ are formyl, dimethoxymethyl, diethoxymethyl and dibutoxymethyl, and examples of meanings for $R^2$ are methyl, ethyl, n-propyl, isopropyl, n-butyl, sec-butyl, isobutyl, tert-butyl or the corresponding alkoxy substituents, or cyclopropyl.

Suitable salts of compounds of the formula I are agriculturally utilizable salts, such as alkali metal salts, especially potassium or sodium salts, alkaline earth metal salts, especially calcium, magnesium and barium salts, manganese, copper, zinc and iron salts, and ammonium, phosphonium, sulfonium, and sulfoxonium salts, for example ammonium, tetraalkylammonium, benzyltrialkylammonium, trialkylsulfonium and trialkylsulfoxonium salts.

The cyclohexenone derivatives of the formula I may be obtained by reacting a corresponding compound of the formula II

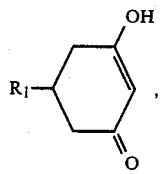

in conventional manner with an acid chloride $R^2$-COCl, for example by means of triethylamine, pyridine, sodium hydroxide or potassium carbonate, to give the enol ester, followed by rearrangement with an imidazole or pyridine base, e.g., 4-N,N-dimethylaminopyridine.

If an acetal, i.e., a compound in which $R^1$ is CH(OR$^3$)$_2$, has initially been prepared in this manner, the free aldehyde ($R^1$=—CHO) may of course be obtained by means of an acid such as hydrochloric acid, sulfuric acid, phosphoric acid, formic acid, acetic acid and oxalic acid, in a solvent such as tetrahydrofuran, 1,4-dioxane, dichloromethane, methanol, ethanol and toluene.

It is also possible initially to prepare a corresponding thioacetal and to saponify it in accordance with

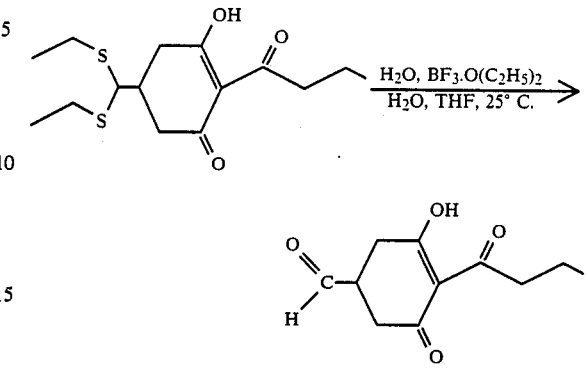

This reaction succeeds for example in the presence of a mercury salt and boron fluoride etherate, as mentioned above.

The precursors required for the reaction may be obtained in accordance with the following scheme:

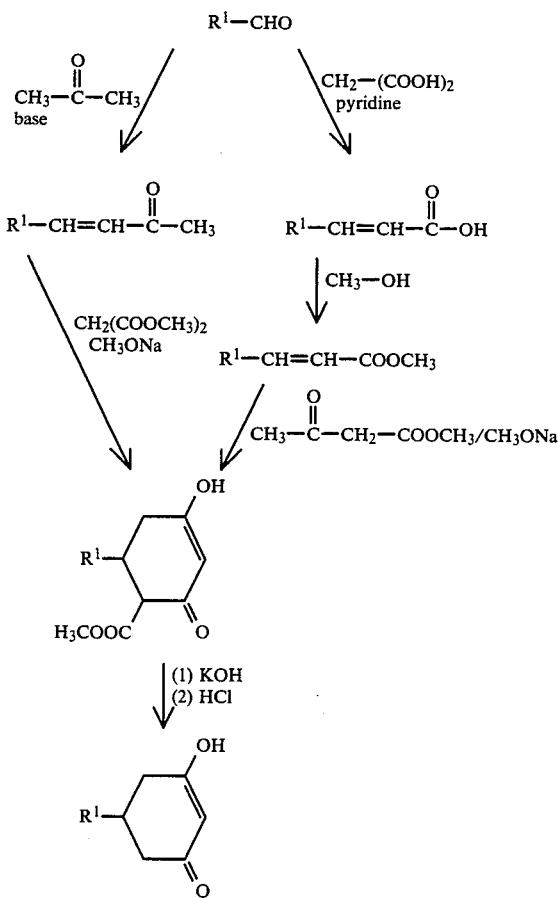

The $^1$H-NMR spectra of the compounds given below were recorded using deuterochloroform as solvent and tetramethylsilane as internal standard. The $^1$H chemical shifts are given in (ppm), only characteristic signals being listed. The abbreviations in the table below have the following meanings:

s=singlet, d=doublet, t=triplet, q=quartet, m=multiplet.

EXAMPLE 1

3.16 g of 5-bis(ethylthio)-methyl-2-butyryl-3-hydroxycyclohex-2-en-1-one in 10 ml of tetrahydrofuran was dripped into a mixture of 4.33 g of mercury(II) oxide, 2.84 g of boron trifluoride etherate, 50 ml of tetrahydrofuran and 330 ml of water. After 30 minutes the mixture was filtered, and the filtrate was extracted twice with diethyl ether, concentrated and chromatographed over silica gel. There was obtained 3.0 g (86% of theory) of 2-butyryl-5-formyl-3-hydroxycyclohex-2-en-1-one:

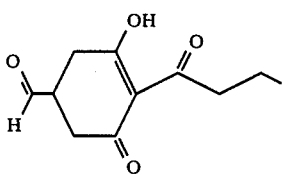

(compound no. 1 in the table below)
$^1$H—NMR: 0.98 (t); 1.65 (m); 2.55–2.95 (m); 3.01 (t); 9.77 (s); 16.7 (s).

EXAMPLE 2

1.1 g of 2-butyryl-5-formyl-3-hydroxycyclohex-2-en-1-one, 0.6 g of trimethyl orthoformate, 50 ml of methanol and 0.05 g of an acidic ion exchanger were refluxed for 2 hours. After the mixture had cooled it was diluted with 100 ml of diethyl ether and filtered through a thin layer of silica gel. After concentration of the filtrate, there remained 0.9 g of 5-bis(methoxy)-methyl-2-butyryl-3-hydroxycyclohex-2-en-1-one as an oil.

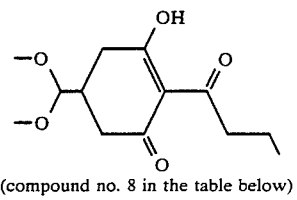

(compound no. 8 in the table below)

TABLE

| No. | $R^1$ | $R^2$ | Characteristic $^1$H—NMR data or melting points |
|---|---|---|---|
| 1 | —CHO | n-$C_3H_7$ | 0.98 (t); 1.65 (m); 3.01 (t); 9.77 (s); 16.7 (s) |
| 2 | —CHO | $C_2H_5$ | 1.17 (t); 3.09 (q); 9.73 (s) |
| 3 | —CHO | $CH_3$ | |
| 4 | —CHO | n-$C_4H_9$ | |
| 5 | —CHO | i-$C_3H_7$ | |
| 6 | —CH(OCH$_3$)$_2$ | $CH_3$ | |
| 7 | —CH(OCH$_3$)$_2$ | $C_2H_5$ | 1.25 (t); 3.12 (q); 3.40 (s) |
| 8 | —CH(OCH$_3$)$_2$ | n-$C_3H_7$ | 0.97 (t); 3.40 (s); 4.12 (d) |
| 9 | —CH(OCH$_3$)$_2$ | i-$C_3H_7$ | |
| 10 | —CH(OCH$_3$)$_2$ | n-$C_4H_9$ | |
| 11 | —CH(OC$_2$H$_5$)$_2$ | $C_2H_5$ | |
| 12 | —CH(OC$_2$H$_5$)$_2$ | n-$C_3H_7$ | 0.98 (t); 3.71 (q); 4.30 (d) |
| 13 | —CH(OC$_4$H$_9$)$_2$ | $C_2H_5$ | |
| 14 | —CH(OC$_4$H$_9$)$_2$ | -n-$C_3H_7$ | 2.99 (t); 3.62 (t); 4.30 (d) |
| 15 | —CHO | n-$C_3H_7$ sodium salt | 92–95° C. |
| 16 | —CHO | n-$C_3H_7$ potassium salt | 140° C. (decomp.) |
| 17 | —CHO | n-$C_3H_7$ tetrabutylammonium salt | |
| 18 | —CH(OCH$_3$)$_2$ | n-$C_3H_7$ sodium salt | 160° C. (decomp.) |
| 19 | —CH(OCH$_3$)$_2$ | n-$C_3H_7$ potassium salt | 80° C. (decomp.) |
|  |  |  | Characteristic $^1$H—NMR data or melting prints |
| 20 | —CH(OCH$_3$)$_2$ | n-$C_3H_7$ tetrabutylammonium salt | 0.93 (t); 3.23 (s); 4.08 (d) |
| 21 | —CHO | cyclopropyl | |
| 22 | —CHO | methoxyethyl | |
| 23 | —CHO | $C_2H_5$ | 110–112° C. |
| 24 | —CHO | $C_2H_5$ potassium salt | 127–129° C. |
| 25 | —CH(OCH$_3$)$_2$ | $C_2H_5$ sodium salt | 103–114° C. |

The cyclohexenone derivatives of the formula I may have a variety of influences on virtually all development stages of a plant, and are therefore used as growth regulators.

To determine the growth-regulating properties of the candidate compounds, a culture medium was supplied with sufficient nutrients, and test plants were grown therein in plastic pots approx. 12.5 cm in diameter and having a volume of about 500 ml).

For the soil treatment, the candidate compounds were applied as aqueous formulations either on the day of sowing (preemergence treatment) or after germination (postemergence treatment).

In foliage applications, the candidate compounds were sprayed as aqueous formulations onto the plants (postemergence foliage treatment).

The commercial growth regulator chlormequat chloride (CCC) was used for comparison purposes.

The growth-regulating action observed was confirmed at the end of the experiment by measuring the growth height. The figures obtained were compared with those for untreated plants. Not only was growth height reduced—the leaves also took on a more intense color. The increased chlorophyll content is indicative of a higher rate of photosynthesis, making for bigger yields.

The individual data are given in the following tables:

TABLE 1

Spring wheat, "Kolibri" variety
Postemergence foliage treatment

| Ex. no. | Conc. mg of active ingredient per vessel | Growth height |
| --- | --- | --- |
| untreated | — | 100 |
| CCC | 6 | 69.0 |
| 1 | 6 | 64.4 |
| 2 | 6 | 61.8 |
| 7 | 6 | 75.5 |
| 8 | 6 | 67.6 |
| 15 | 6 | 86.4 |
| 16 | 6 | 69.2 |
| 18 | 6 | 92.7 |
| 19 | 6 | 75.4 |
| 20 | 6 | 81.7 |

TABLE 2

Spring barley, "Aramir" variety
Postemergence foliage treatment

| Ex. no. | Conc. mg of active ingredient per vessel | Growth height |
| --- | --- | --- |
| untreated | — | 100 |
| CCC | 6 | 79.6 |
| 1 | 6 | 58.9 |
| 2 | 6 | 73.6 |
| 7 | 6 | 78.4 |
| 8 | 6 | 68.7 |
| 15 | 6 | 92.5 |
| 16 | 6 | 71.6 |
| 18 | 6 | 86.6 |
| 19 | 6 | 73.1 |
| 20 | 6 | 88.1 |

TABLE 3

Spring barley, "Aramir" variety
Preemergence application to the soil

| Ex. no. | Conc. mg of active ingredient per vessel | Growth height |
| --- | --- | --- |
| untreated | — | 100 |
| CCC | 6 | 80.8 |
| 1 | 6 | 60.1 |
| 2 | 6 | 53.5 |
| 23 | 6 | 76.6 |

TABLE 4

Rice, "Nihonbare" variety
Postemergence foliage treatment

| Ex. no. | Conc. mg of active ingredient per vessel | Growth height |
| --- | --- | --- |
| untreated | — | 100 |
| CCC | 1.5 | 99.8 |
|  | 6 | 99.8 |
| 1 | 1.5 | 72.3 |
|  | 6 | 37.9 |

We claim:

1. Cyclohexenone derivatives of the formula

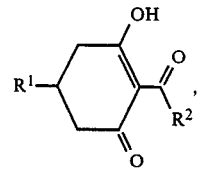

where $R^1$ is —CHO or —CH(OR$^3$)$_2$, $R^2$ is alkyl or alkoxyalkyl, each of 1 to 4 carbon atoms, or cyclopropyl, and $R^3$ is alkyl of 1 to 8 carbon atoms, and salts thereof.

2. A composition for regulating plant growth, which comprises: an effective amount of at least one cyclohexenone derivative of the formula I as set forth in claim 1 and a liquid or solid carrier.

3. A process for regulating the growth of plants, which comprises: contacting the plants or their habitat with an effective amount of at least one cyclohexenone derivative of the formula I as set forth in claim 1.

4. A cyclohexenone derivative of formula I as set forth in claim 1, where $R^1$ is —CHO.

5. A cyclohexenone derivative of formula I as set forth in claim 1, where $R^1$ is —CHO and $R^2$ is n-propyl.

6. A cyclohexenone derivative of formula I as set forth in claim 1, where $R^1$ is —CHO and $R^2$ is ethyl.

7. A composition as defined in claim 6 which also includes a surfactant.

* * * * *